US00PP08402P

United States Patent [19]

Warriner

[11] Patent Number: Plant 8,402

[45] Date of Patent: Oct. 5, 1993

[54] ROSE PLANT JACLIANG

[75] Inventor: William A. Warriner, Tustin, Calif.

[73] Assignee: Bear Creek Gardens, Inc., Medford, Oreg.

[21] Appl. No.: 795,959

[22] Filed: Nov. 21, 1991

[51] Int. Cl.[5] ..... A01H 5/00

[52] U.S. Cl. ..... Plt./9

[58] Field of Search ..... Plt. 9, 10, 19, 20, Plt./27, 28

*Primary Examiner*—Howard J. Locker
*Assistant Examiner*—E. F. McElwain
*Attorney, Agent, or Firm*—Klarquist, Sparkman, Campbell, Leigh & Whinston

[57] ABSTRACT

A miniature rose from a cross of an unnamed white flowered seedling with the variety Angel Face (U.S. Plant Pat. No. 2,792) possesses plum-colored flowers and dark green, glossy, small leaves. The variety is easily propagated with softwood cuttings.

1 Drawing Sheet

The present invention relates to a new and distinct variety of rose plant of the miniature class which was originated by me by crossing an unnamed seedling, with the variety Angel Face, U.S. Plant Pat. No. 2,792.

The primary objective of this breeding was to produce a new rose variety having the miniature flowers, leaves and habit of the unnamed white flowered seedling combined with the plum colored flowers of the variety Angel Face. The objective was substantially achieved along with other desirable improvements as evidenced by the following unique combination of characteristics which are outstanding in the new variety and which distinguish it from its parents, as well as from all other varieties of which I an aware:

1. Small, plum colored flowers
2. Moderate pleasing fragrance
3. Ease of production from softwood cuttings
4. Dark green glossy small leaves Asexual reproduction of this new variety by budding and soft wood cuttings, as performed at Wasco and Somis, Calif., whows that the foregoing characteristics and distinctions come true to form and are established and transmitted through succeeding propagations.

The accompanying photograph shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—Angel Face.

Classification:

*Botanical.*—Rosa hybrida.

*Commercial.*—Miniature.

FLOWER

Observations made from specimens grown in a garden environment in Somis, Calif. in May-August of 1991.

Blooming Habit: Continuous.

Bud:

*Size.*—½ inch when the petals start to unfurl.

*Form.*—Short, pointed ovoid.

*Color.*—When sepals first divide, bud color is red Group 53B. When half blown, the upper sides of the petals are Red Group 53D; and the lower sides of the petals are Red Group 53D.

*Sepals.*—Color: Green Group 138C. Surface texture: Covered with fine hairs. There are three lightly to normally appendaged sepals. there are two unappendaged sepals with hairy edges.

*Receptacle.*—Color: Green Group 137C, sometimes with a bronze overcast. Shape: Funnel. Size: Small, ¼"×1974". Surface: Smooth.

*Peduncle.*—Length: Short, 1 to ½ inches. Surface: Smooth. Color: Bronzy. Strength: Stiff, erect, slender.

Bloom:

*Size.*—Small. Average open size is 2 to 2½ inches.

*Borne.*—Several together, in pyramidal clusters.

*Stems.*—Short, strong.

*Form.*—When first open: High centered to globular. Permanence: Flattens, outer petals curl back.

*Petalage.*—Number of petals under normal conditions: 25-30.

*Color.*—The upper side of the petals is Red Group 53D. The reverse side of the petals is Red Group 53D. The base of petals has a small white half moon at the point of attachment. The major color on the upper side is Red Group 53D.

*Variegations.*—Occassional white streak on the guard petals.

*Discoloration.*—The general tonality at the end of the first day: No change. At the end of the third day, No change.

*Fragrance.*—Moderate.

Petals:

*Texture.*—Thick.

*Shape.*—Notched, deltoid.

*Form.*—Tips slightly recurved.

*Arrangement.*—Imbricated, with a few petaloids in the center.

*Persistence.*—Hang on and dry.

*Lastingness.*—On the plant: Fair, 4-5 days. As a cut flower: Fair, 5-6 days.

Reproductive parts:

*Anthers.*—Size: Large. Quantity: Many. Color: Yellow. Arrangement: Regular around styles.

*Filaments.*—Color: Reddish brown.

*Pollen.*—Color: Gold-yellow.

*Styles.*—Color: Greenish-white.

*Stigmas.*—Color: Greenish-white.

Form: Bush.

Growth: Vigorous; dwarf; compact.

Foliage: Number of leaflets on normal mid-stem leaves: 5.

*Size.*—Small, 2 to 2½" long × 1½ wide.

*Quantity.*—Normal.

*Color.*—New foliage: Reddish. Old foliage: Dark glossy green.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Rough, with prickles.

*Stipules.*—Short, bearded.

*Diseased resistance.*—Susceptible to mildew under normal growing conditions but resistant to rust at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium hooked slightly downward.

*Color when young.*—Red.

Small prickles:

*Quantity.*—On main stalks: None. On laterals: None.

I claim:

1. A new and distinct variety of rose plant of the miniature rose class, substantially as herein shown and described, characterized particularly as to novelty by the unique combination of its distinctive small, dark green glossy foliage, its moderate pleasing fragrance, its ease of propagation from softwood cuttings and its unique plum colored flowers.

* * * * *

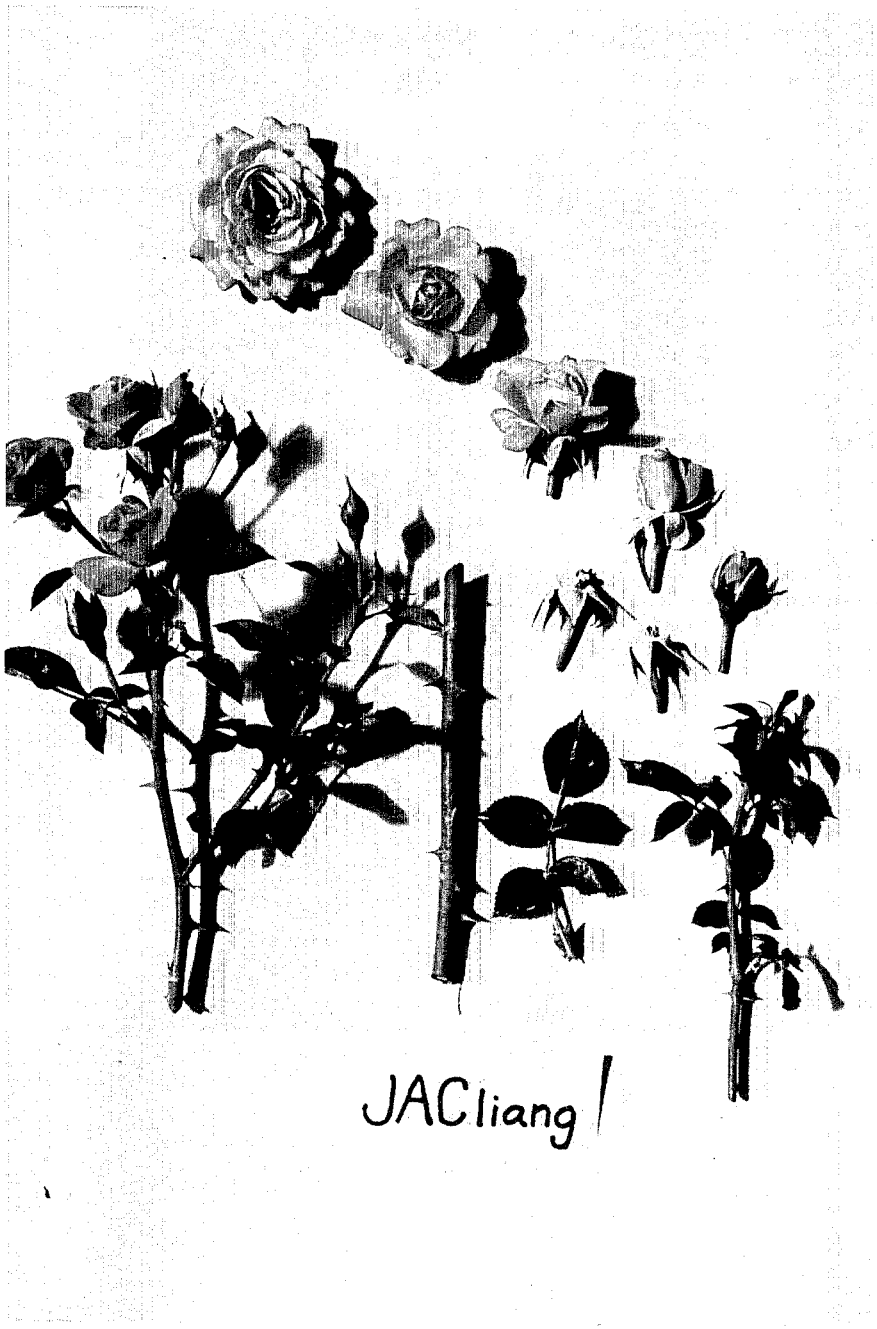
JACliang